US006465496B1

(12) United States Patent
Aronhime et al.

(10) Patent No.: US 6,465,496 B1
(45) Date of Patent: Oct. 15, 2002

(54) TORSEMIDE POLYMORPHS

(75) Inventors: Judith Aronhime; David Leonov, both of Rehovot; Marko Kordova, Kfar Saba; Anchel Schwartz, Rehovot; Ben-Zion Dolitzky, Petach Tiqva, all of (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 48 days.

(21) Appl. No.: 09/638,106

(22) Filed: Aug. 11, 2000

Related U.S. Application Data (60) Provisional application No. 60/148,305, filed on Aug. 11, 1999, provisional application No. 60/183,127, filed on Feb. 17, 2000, and provisional application No. 60/215,273, filed on Jun. 30, 2000.

(51) Int. Cl.[7] ........................ A61K 31/44; C07D 213/71
(52) U.S. Cl. ........................ 514/347; 546/294; 546/293; 546/291; 514/346
(58) Field of Search ................................ 514/347, 346, 514/294, 293, 291

(56) References Cited

U.S. PATENT DOCUMENTS

| 4,018,929 A | 4/1977 | Delarge et al. |
|---|---|---|
| 4,055,650 A | 10/1977 | Delarge et al. |
| RE30,633 E | 6/1981 | Delarge et al. |
| 4,743,693 A | 5/1988 | Topfmeier et al. |
| 4,822,807 A | 4/1989 | Topfmeier et al. |
| 4,861,786 A | 8/1989 | Demmer et al. |
| RE34,580 E | 4/1994 | Topfmeier et al. |
| RE34,672 E | 7/1994 | Topfmeier et al. |
| 5,914,336 A | 6/1999 | Dreckmann-Behrendt |
| 6,166,045 A | * 12/2000 | Dreckmann-Behrendt et al. ............ 514/347 |

OTHER PUBLICATIONS

DuPont, P. et al. "Structure d'une Seconde Variété de la Torasémide," Acta Cryst. (1978). B34, pp. 2659–2662.
DuPont, P., Structure Cristalline et Moléculaire d'un Diurétique Dérivé de l'Alkyl–1 [(Phénylamino–4 pyridyl–3) sulfonyl]–3 Urée: la Torasémide ($C_{15}H_{20}N_4SO_3$), Acta Cryst. (1978).B34, pp. 1304–1310.

* cited by examiner

Primary Examiner—Charanjit S. Aulakh
(74) Attorney, Agent, or Firm—Kenyon & Kenyon (57) ABSTRACT

The present invention is directed to the novel forms of torsemide, designated Form V, amorphous torsemide, Dupont Form 2 solvent adduct, Dupont Form 2 ethanol adduct and Dupont Form 2 isopropanol adduct. Methods for their preparation are also disclosed. The present invention also relates to processes for making torsemide modification I. Pharmaceutical compositions containing the new forms of torsemide and methods of using them are also disclosed.

91 Claims, 9 Drawing Sheets

TORSEMIDE POLYMORPHS

CROSS-REFERENCE TO RELATED APPLICATIONS

This application claims the benefit of provisional application Ser. No. 60/148,305, filed Aug. 11, 1999; provisional application Ser. No. 60/183,127, filed Feb. 17, 2000; and provisional application Ser. No. 60/215,273, filed Jun. 30, 2000. All three of these applications are incorporated herein by reference.

FIELD OF THE INVENTION

The present invention relates to novel polymorphic forms of torsemide and amorphous torsemide. The present invention also relates to methods of making polymorphic forms of torsemide. The present invention also relates to methods of making solvent adducts of torsemide.

BACKGROUND OF THE INVENTION

1-Isopropyl-3-[(4-m-toluidino-3-pyridyl) sulfonyl]urea, which has the chemical structure is approved, under the trademark DEMADEX®, by the U.S. Food and Drug Administration for the treatment of hypertension and edema associated with congestive heart failure, renal disease, or hepatic disease. The USAN approved generic name for this compound is torsemide, although this compound is also referred to as "torasemide" in the art. Torsemide is a loop diuretic that has been found to be particularly effective for the treatment of edema associated with chronic renal failure.

U.S. Pat. No. Re. 30,633 describes a synthesis of torsemide. It is known that torsemide can occur in at least two different crystalline forms, Acta Cryst. 1978, pp. 2659–2662 and Acta Cryst., 1978, pp. 1304–1310, in which the crystal identified by space group P21/c is designated Dupont Form 1 herein and the crystal identified by space group P2/n is designated Dupont Form 2 herein. U.S. Pat. No. 4,822,807, which reissued as U.S. Pat. No. Re. 34,672, describes two crystalline forms of torsemide, designated modification I and modification II. Torsemide modification I is defined herein as the torsemide characterized by the x-ray powder diffraction pattern of FIG. 1, in the 37 C.F.R. § 1.132 declaration by Dr. Fritz Topfmeier filed on Dec. 30, 1987, which is located in the file wrapper of U.S. Pat. No. 4,822,807 (the "Topfmeier Declaration"). Torsemide modification II is defined herein as the torsemide characterized by the x-ray powder diffraction pattern of FIG. 2, in the Topfmeier Declaration. U.S. Pat. No. 5,914,336 describes a crystalline form of torsemide designated modification III, herein designated as "the '336 modification III." PCT Publication WO 00/20395 describes a crystalline form of torsemide also designated modification III, which herein is designated as "Pliva modification III."

Dupont reports in Acta Crystallographica (1978) B34, 2659–2662, a torsemide polymorph with unit cell dimensions (in angstroms) a=20.446, b=11.615, c=16.877, a space group of P2/n and tabulated x-ray data crystal data therein, which herein is designated "Dupont Form 2". The reference Acta Crystallographica (1978) B34, 2659–2662 is incorporated herein by reference.

SUMMARY OF THE INVENTION

The existence of new forms of torsemide has now been discovered. They are designated torsemide Form V and amorphous torsemide. New solvent adducts of Dupont Form 2 have been discovered including an ethanol solvent adduct and an isopropanol solvent adduct, both of which have x-ray powder diffraction patterns which correspond to torsemide Dupont Form 2.

New processes for the preparation of torsemide modification I have also been discovered. New processes of the present invention include the preparation of torsemide modification I from torsemide modification II or from mixtures of torsemide modification II and modification I. The processes of the present invention provides more efficient and quicker methods for making pure torsemide modification I.

The present invention relates to a process for making torsemide Dupont Form 2 comprising the steps of: (a) suspending torsemide in water; (b) basifying the torsemide suspension of step (a) with sufficient base to substantially dissolve the torsemide; (c) adding an organic solvent to the resulting torsemide solution in an amount sufficient to induce the formation of torsemide Dupont Form 2; (d) adding an acid to the torsemide solution of step (c) until torsemide Dupont Form 2 begins to precipitate; and (e) isolating torsemide Dupont Form 2

The present invention also relates to a pharmaceutical composition comprising torsemide Dupont Form 2 and a pharmaceutically acceptable carrier.

The present invention also relates to a method for treating edema comprising the step of administering to a patient in need of such treatment a therapeutically effective amount of the torsemide Dupont Form 2.

The present invention also relates to processes for making torsemide Dupont Form 2 solvent adduct comprising the steps of: (a) suspending torsemide in water; (b) basifying the torsemide suspension of step (a) with sufficient base to substantially dissolve the torsemide; (c) adding an organic solvent to the resulting torsemide solution in an amount sufficient to induce the formation of torsemide Dupont Form 2 solvent adduct; (d) adding an acid to the torsemide solution of step (c) until torsemide Dupont Form 2 solvent adduct begins to precipitate; and (e) isolating torsemide Dupont Form 2 solvent adduct.

The present invention also relates to torsemide Dupont Form 2 solvent adducts.

The present invention also relates to torsemide Dupont Form 2 isopropanol adduct.

The present invention also relates to torsemide Dupont Form 2 ethanol adduct.

The present invention also relates to a torsemide solvent adduct wherein the solvent content is up to about 2.5% by weight.

The present invention also relates to torsemide Dupont Form 2 isopropanol adduct which is characterized by a powder x-ray diffraction pattern comprising peaks at about 6.0±0.2, 9.2±0.2, 9.7±0.2, 11.3±0.2, 12.0±0.2, 15.8±0.2, 18.4±0.2, 19.7±0.2, 20.4±0.2, 22.6±0.2, 23.5±0.2, 25.5±0.2, and 27.5±0.2 degrees two-theta.

The present invention also relates to a pharmaceutical composition comprising the torsemide Dupont Form 2 ethanol adduct and a pharmaceutically acceptable carrier.

The present invention also relates to a pharmaceutical composition comprising the torsemide Dupont Form 2 isopropanol adduct and a pharmaceutically acceptable carrier.

The present invention also relates to a pharmaceutical composition comprising the torsemide Dupont Form 2 solvent adduct and a pharmaceutically acceptable carrier.

The present invention also relates to a method for treating edema comprising the step of administering to a patient in need of such treatment a therapeutically effective amount of the torsemide Dupont Form 2 isopropanol adduct.

The present invention also relates to a method for treating edema comprising the step of administering to a patient in need of such treatment a therapeutically effective amount of the torsemide Dupont Form 2 ethanol adduct.

The present invention also relates to a method for treating edema comprising the step of administering to a patient in need of such treatment a therapeutically effective amount of the torsemide Dupont Form 2 solvent adduct.

The present invention also relates to processes for making torsemide Dupont Form 2 ethanol adduct from amorphous torsemide comprising the steps of: (a) suspending amorphous torsemide in ethanol; (b) heating the suspension to 80° C. ; and (c) isolating torsemide Dupont Form 2 ethanol adduct.

The present invention also relates to processes for making torsemide modification I from torsemide Dupont Form 2 comprising the steps of: suspending torsemide Dupont Form 2 in water at pH 5; and isolating torsemide modification I.

The present invention also relates to processes for making torsemide Form V comprising the steps of: (a) suspending torsemide in a solvent; (b) increasing the pH of the torsemide suspension with base sufficient to substantially dissolve the torsemide; (c) precipitating torsemide Form V from the resulting solution; and (d) isolating torsemide Form V.

The present invention also relates to the new form of torsemide: torsemide Form V.

The present invention also relates to torsemide which is characterized by a powder x-ray diffraction pattern comprising peaks at about: 5.9±0.2, 8.4±0.2, 12.0±0.2, 12.5±0.2, 13.30±0.2, 16.0±0.2, 17.7±0.2, 19.9±0.2, 21.5±0.2, 22.7±0.2, 24.0±0.2, 24.7±0.2 degrees two-theta.

The present invention also relates to a pharmaceutical composition comprising the torsemide Form V and a pharmaceutically acceptable carrier.

The present invention also relates to a method for treating edema comprising the step of administering to a patient in need of such treatment a therapeutically effective amount of the torsemide Form V.

The present invention also relates to processes for making amorphous torsemide comprising the steps of: (a) suspending torsemide in water; (b) treating the torsemide suspension of step (a) with ammonium hydroxide or ammonia gas sufficient to completely dissolving the torsemide; (c) cooling the torsemide solution of step (b); and isolating amorphous torsemide by lyophilization.

The present invention also relates to amorphous torsemide, which is characterized by a broad x-ray diffraction maxima at about 14 to 26 degrees two-theta and an IR spectrum comprising bands at 833, 899, 1044, 1080, 1125, 1146, 1236, 1267, 1489, 1516, 1585, 1644, 1700 cm$^{-1}$.

The present invention also relates to a pharmaceutical composition comprising the amorphous torsemide and a pharmaceutically acceptable carrier.

The present invention also relates to a method for treating edema comprising the step of administering to a patient in need of such treatment a therapeutically effective amount of the amorphous torsemide.

The present invention also relates to processes for making torsemide modification I from torsemide comprising the steps of: (a) adding torsemide to a solvent mixture comprising acetonitrile; and (b) isolating torsemide modification I.

The present invention also relates to processes for making torsemide modification I comprising the steps of: (a) adding torsemide to methanol; (b) refluxing the mixture of torsemide and methanol; (c) and isolating torsemide modification I.

The present invention also relates to processes for making torsemide modification II from amorphous torsemide comprising the steps of: (a) suspending amorphous torsemide in water; (b) heating the suspension; and (c) isolating torsemide modification II.

The present invention also relates to processes for making a mixture of torsemide modification I and torsemide modification II from torsemide Form V comprising the steps of: suspending torsemide Form V in water; and isolating a mixture of torsemide modification I and torsemide modification II.

The present invention also relates to processes for making torsemide modification II from amorphous torsemide comprising the steps of: (a) adding amorphous torsemide to water; (b) stirring the torsemide water mixture for a time sufficient to induce the transformation of amorphous torsemide to torsemide modification II; and (c) isolating torsemide modification II.

The present invention also relates to processes for making torsemide modification I from torsemide modification II comprising the steps of: (a) adding torsemide modification II to ethanol; (b) stirring the torsemide ethanol mixture for a time sufficient to induce the transformation of torsemide modification II to torsemide modification I; and (c) isolating torsemide modification I.

The present invention also relates to processes for making torsemide modification I from torsemide modification II comprising the steps of: (a) adding torsemide modification II to dimethyl formnamide; (b) stirring the mixture of torsemide modification II and dimethyl formamide for a time sufficient to induce the transformation of torsemide modification II to torsemide modification I; and (c) isolating torsemide modification I.

DETAILED DESCRIPTION OF THE INVENTION

Torsemide Dupont Form 2 and Torsemide Dupont Form 2 Solvent Adduct

The present invention relates to new processes for preparing torsemide Dupont Form 2. Torsemide designated Dupont Form 2 is prepared as follows. Torsemide is suspended in water, and the pH is raised by the addition of base to allow the torsemide to dissolve. A pH of about 9.5 to about 10.5 is a suitable endpoint. Suitable bases include nitrogenous bases such as ammonium hydroxide, and alkali and alkaline earth metal bases such as sodium hydroxide, potassium hydroxide, magnesium hydroxide, and the like. Preferably the base is sodium hydroxide.

An organic solvent is then added to the torsemide solution with stirring. Suitable solvents include water soluble or partially water soluble alcohols such as propanol, isopropanol and ethanol. Preferably, the solvent is isopropanol or ethanol. The pH of the torsemide solution is then lowered by the addition of a suitable acid until the solution begins to become cloudy and torsemide Dupont Form 2 begins to precipitate. Torsemide begins to precipitate at about pH 6. Suitable acids include acetic acid, hydrochloric acid, sulfuric acid, mineral acids and the like. Acetic acid is preferred. Since torsemide is known to decompose at pH 3.0, the pH of the solution is preferably maintained at about 6±0.1 with a minimum pH of 2±0.5 and a maximum pH of 7.5±0.5. Torsemide Dupont Form 2 is then isolated by filtration and drying to remove solvent.

It has been discovered that torsemide Dupont Form 2 can exist as a solvent adduct. The present invention relates to torsemide Dupont Form 2 solvent adducts and methods for preparing torsemide Dupont Form 2 solvent adducts. Torsemide designated Dupont Form 2 solvent adduct is prepared as follows. Torsemide is suspended in water, and the pH is raised by the addition of base to allow the torsemide to dissolve. A pH of about 9.5 to about 10.5 is a suitable endpoint. Suitable bases include nitrogenous bases such as ammonium hydroxide, and alkali and alkaline earth metal bases such as sodium hydroxide, potassium hydroxide, magnesium hydroxide, and the like. Preferably the base is sodium hydroxide.

An organic solvent is then added to the torsemide solution with stirring. Suitable solvents include water soluble or partially water soluble alcohols such as propanol, isopropanol and ethanol. Preferably, the solvent is isopropanol or ethanol. The pH of the torsemide solution is then lowered by the addition of a suitable acid until the solution begins to become cloudy and torsemide Dupont Form 2 solvent adduct begins to precipitate. Torsemide begins to precipitate at about pH 6. Suitable acids include acetic acid, hydrochloric acid, sulfuric acid, mineral acids and the like. Acetic acid is preferred. Since torsemide is known to decompose at pH 2.0, the pH of the solution is preferably maintained at about 6±0.1 with a minimum pH of 3±0.5 and a maximum pH of 7.5±0.5. Torsemide Dupont Form 2 solvent adduct is then isolated by filtration and drying. In an embodiment of the present invention using ethanol as the organic solvent, torsemide Dupont Form 2 ethanol adduct is isolated. In an embodiment of the present invention using isopropanol as the organic solvent, torsemide Dupont Form 2 isopropanol adduct is isolated.

The present invention also relates to processes for preparing torsemide Dupont Form 2 ethanol adduct from amorphous torsemide. By the processes of the present invention, amorphous torsemide is suspended in ethanol and the suspension is heated to about 50° C. to about 80° C. for a sufficient time to induce the transformation of amorphous torsemide to torsemide Dupont Form 2. Preferably, the suspension is heated to about 80° C. Completion of the conversion is monitored by IR. Preferably, the reaction is heated for about 2 to about 7 hours. More preferably, the reaction is heated for about 7 hours.

Figure 1:
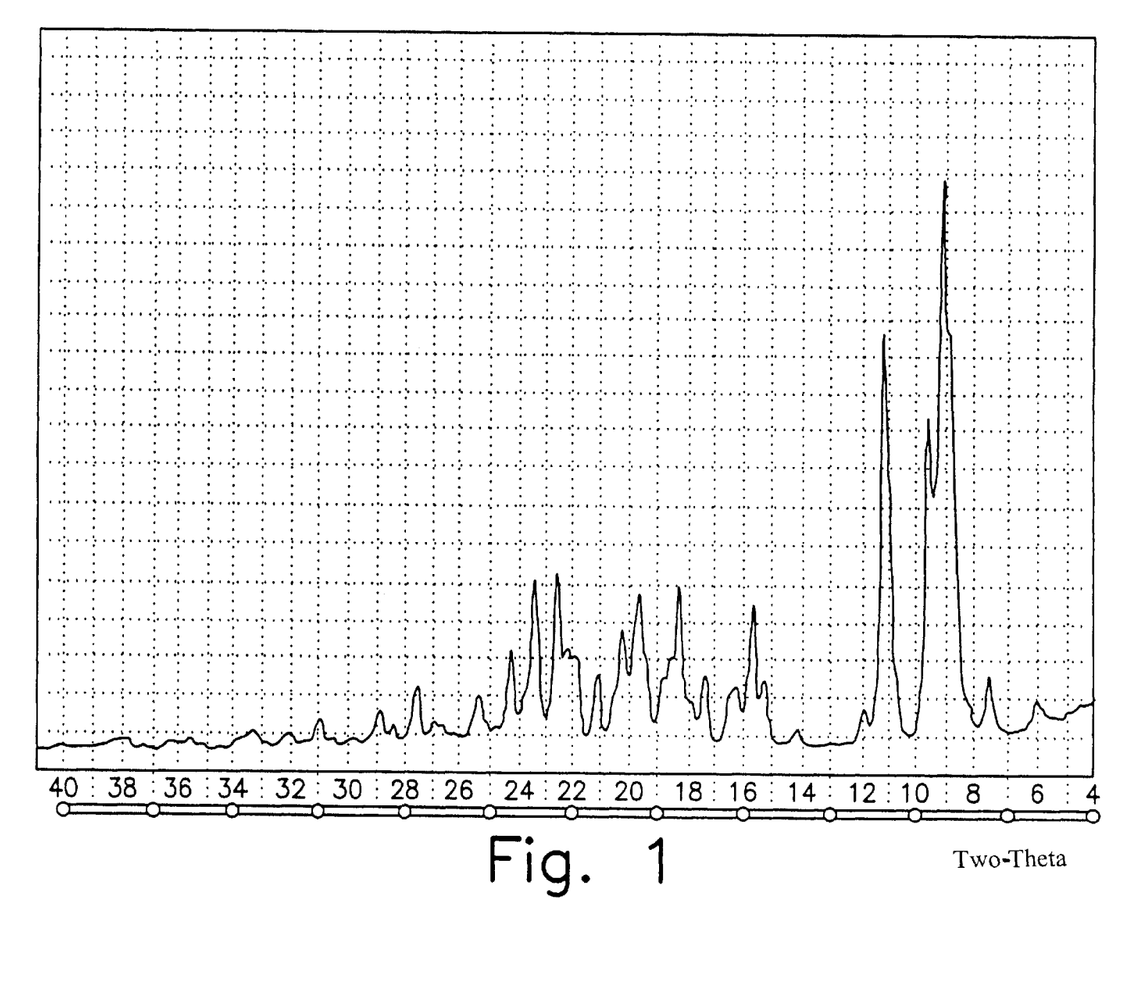
FIG. 1 is a characteristic x-ray powder diffraction spectrum of torsemide Dupont Form 2 isopropanol adduct.

Torsemide Dupont Form 2 isopropanol adduct is characterized by x-ray powder diffraction peaks at 6.0±0.2, 9.2±0.2, 9.7±0.2, 11.3±0.2, 12.0±0.2, 15.8±0.2, 18.4±0.2, 19.7±0.2, 20.4±0.2, 22.6±0.2, 23.5±0.2, 25.5±0.2, 27.5±0.2 degrees two-theta, as shown in FIG. 1. Torsemide Dupont Form 2, torsemide Dupont Form 2 solvent adduct, and torsemide Dupont Form 2 ethanol adduct all have x-ray powder diffraction peaks equivalent to torsemide Dupont Form 2 isopropanol adduct.

Figure 2:
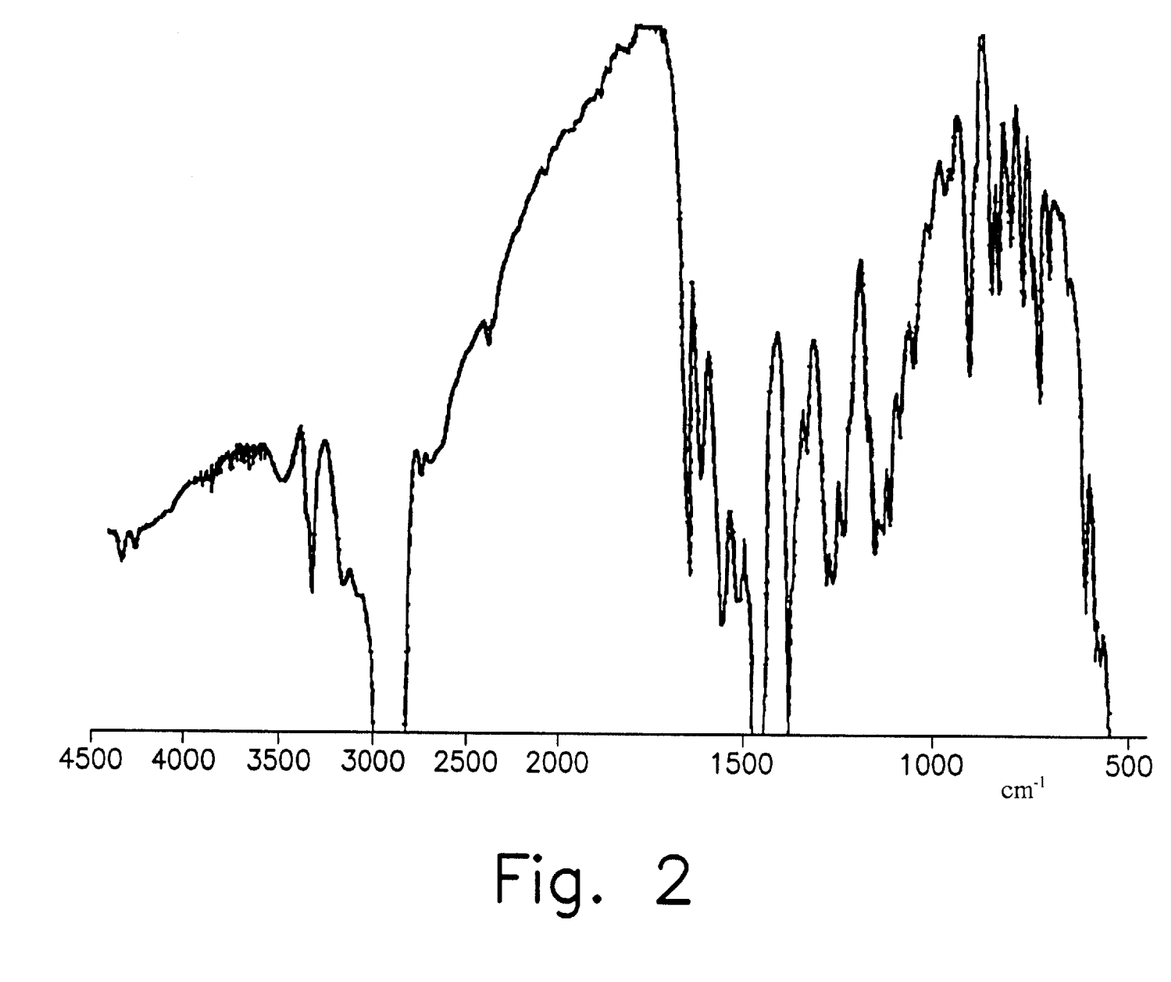
FIG. 2 is a characteristic infrared (IR) absorption spectrum of torsemide Dupont Form 2 solvent adduct.

Torsemide Dupont Form 2 isopropanol adduct is also characterized by IR bands at 738, 762, 791, 821, 838, 900, 1078, 1108, 1150, 1260, 1276, 1321, 1606, 1639 cm$^{-1}$±2, as shown in FIG. 2.

Figure 3:
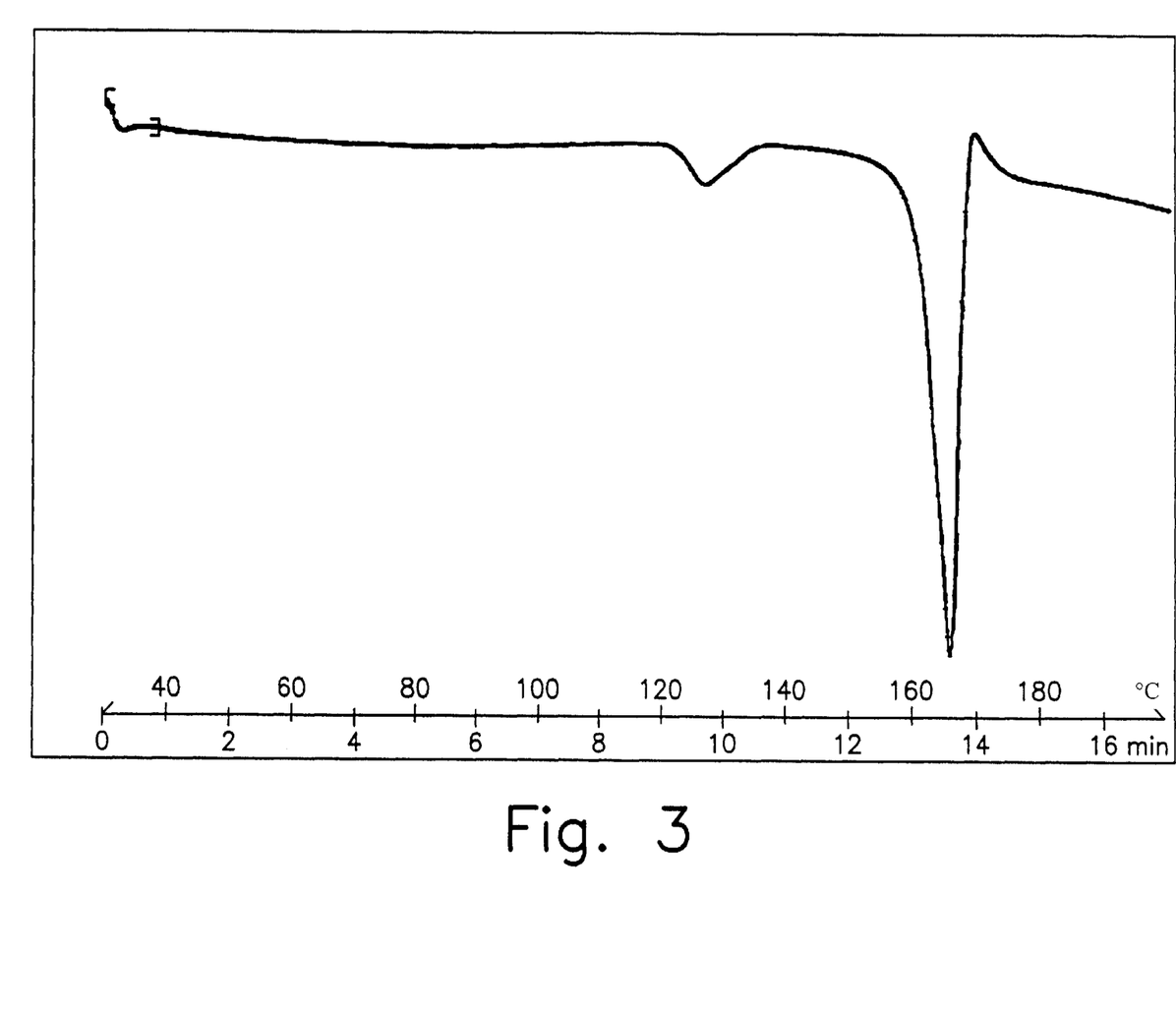
FIG. 3 is a characteristic differential scanning calorimetric (DSC) thermogram of torsemide Dupont Form 2 solvent adduct.
Figure 4:
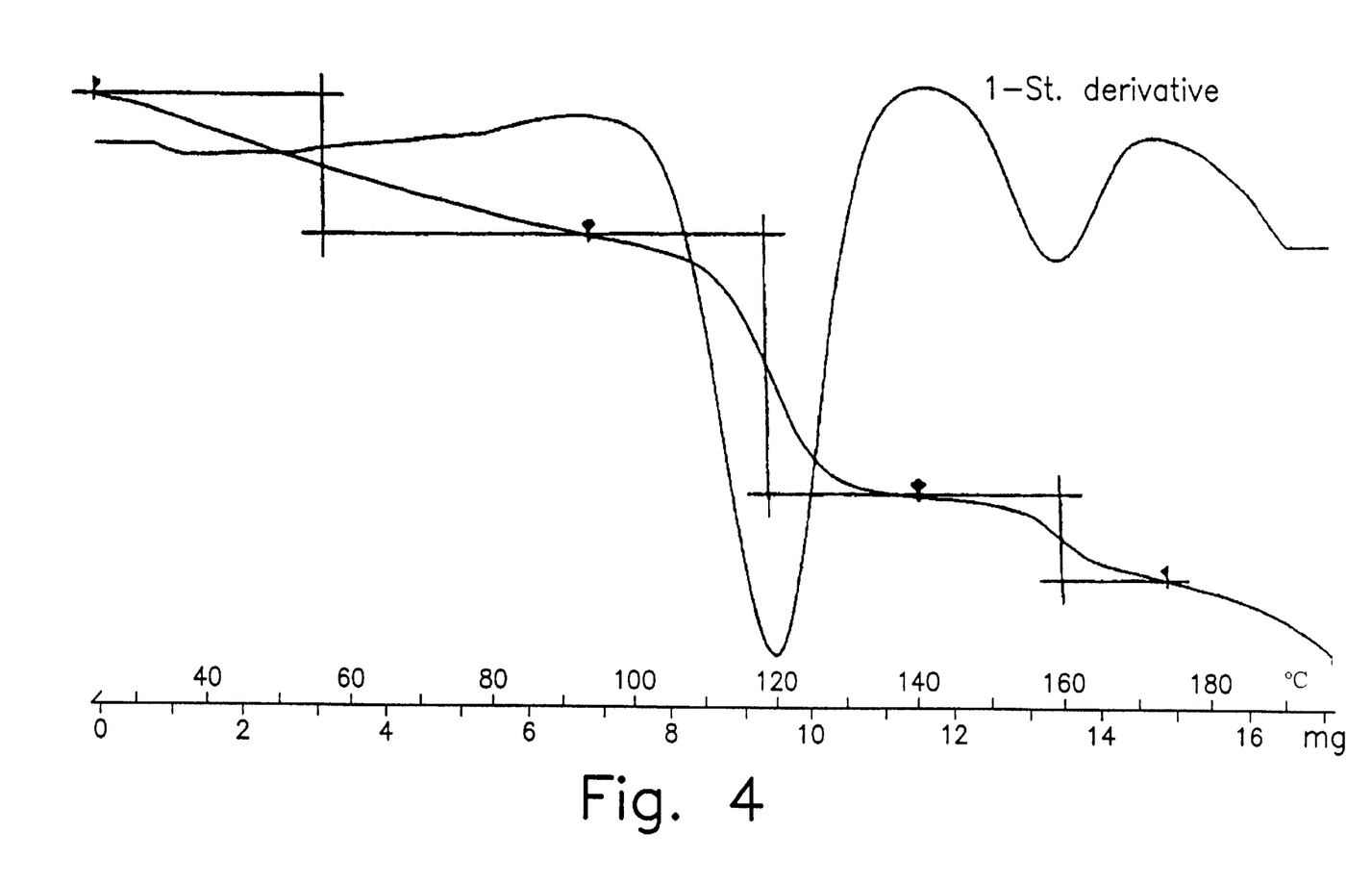
FIG. 4 is a characteristic TGA of torsemide Dupont Form 2 isopropanol adduct.

The differential scanning calorimetric (DSC) thermogram for torsemide Dupont Form 2 solvent adduct is characterized by a small endotherm (about 10–20 J/g) at about 120–130° C. and a melting endotherm with peak temperature at about 165° C. followed by decomposition as shown in FIG. 3. It was found that the torsemide Dupont Form 2 solvent adduct can include up to about 2.5% of a solvent. The torsemide Dupont Form 2 ethanol adduct can include up to 1% of ethanol. The torsemide Dupont Form 2 isopropanol adduct can include up to 2.5% of isopropanol. By TGA (thermogravimetric analysis), the desolvation of the Dupont Form 2 isopropanol adduct occurs at about 120° C. as shown in FIG. 4.

Torsemide used in the present invention to make torsemide Dupont Form 2 may be prepared according to methods known in the art, including methods described in U.S. Pat. No. Re. 30,633, the contents of which are incorporated by reference.

Torsemide Form V

The present invention also relates to a novel torsemide crystalline form designated Form V, and processes for making torsemide Form V. In the method for preparing torsemide Form V, torsemide is dissolved in a solvent. Suitable solvents include water and ethanol. The pH of the solution is raised by the addition of base. Suitable bases include ammonia gas or an ammonia solution such as ammonium hydroxide. The pH is raised until the torsemide dissolves. Preferably the pH is raised to about 10±0.5. The solution is then filtered and the pH of the filtrate is lowered by the addition of acid. Suitable acids include acetic acid. The pH is lowered until precipitation of torsemide Form V begins. Preferably the pH is lowered to about 9±0.5. The torsemide solution is stirred for about 30 minutes. The solution is then filtered and torsemide Form V is isolated upon drying.

It has been found that after the first filtration of the torsemide solution, following the addition of acid, the filtrate may be reduced under a gentle stream of inert gas, which enhances the precipitation of torsemide Form V. Inert gases such as nitrogen, argon and the like may be used. Preferably, the solution is reduced for about 10 minutes. The solution is filtered and dried to yield torsemide Form V.

Figure 5:
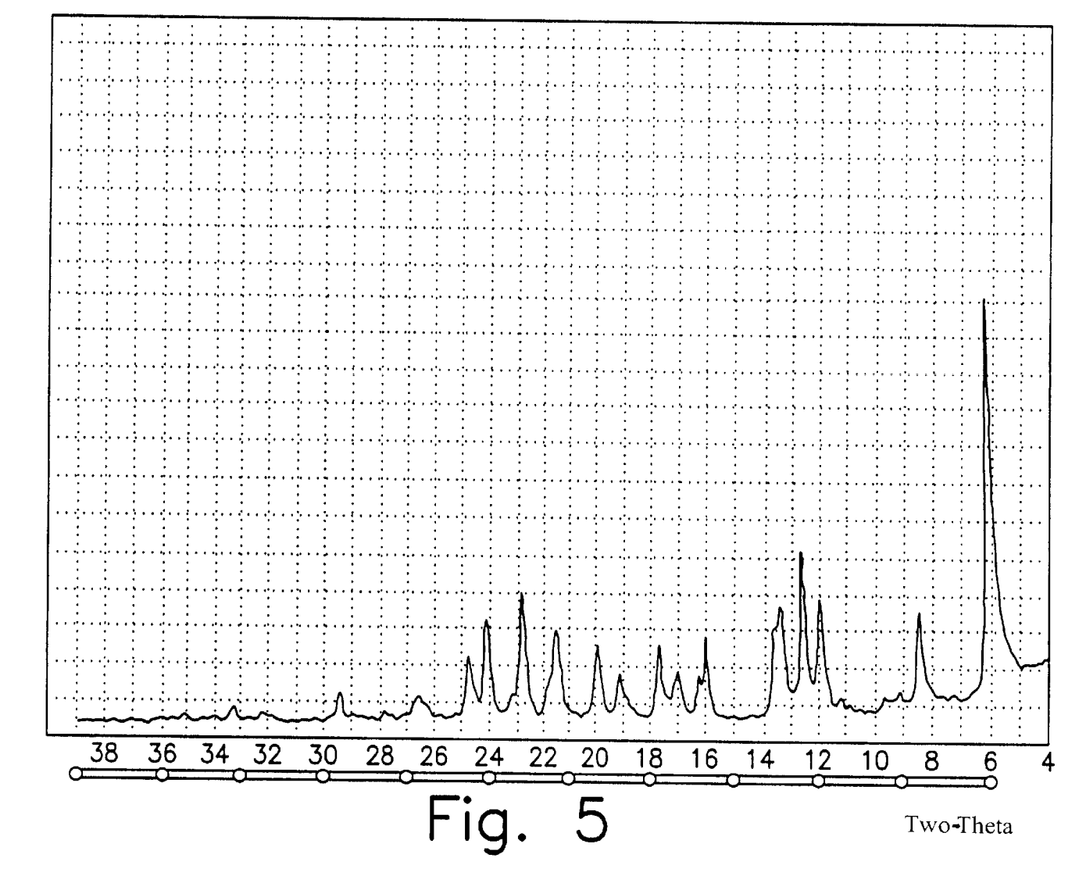
FIG. 5 is a characteristic x-ray powder diffraction spectrum of torsemide Form V.

Torsemide Form V is characterized by x-ray powder diffraction peaks at 5.9±0.2, 8.4±0.2, 12.0±0.2, 12.5±0.2, 13.3±0.2, 16.0±0.2, 17.7±0.2, 19.9±0.2, 21.5±0.2, 22.7±0.2, 24.0±0.2, 24.7±0.2 degrees two-theta, as shown in FIG. 5.

Figure 6:
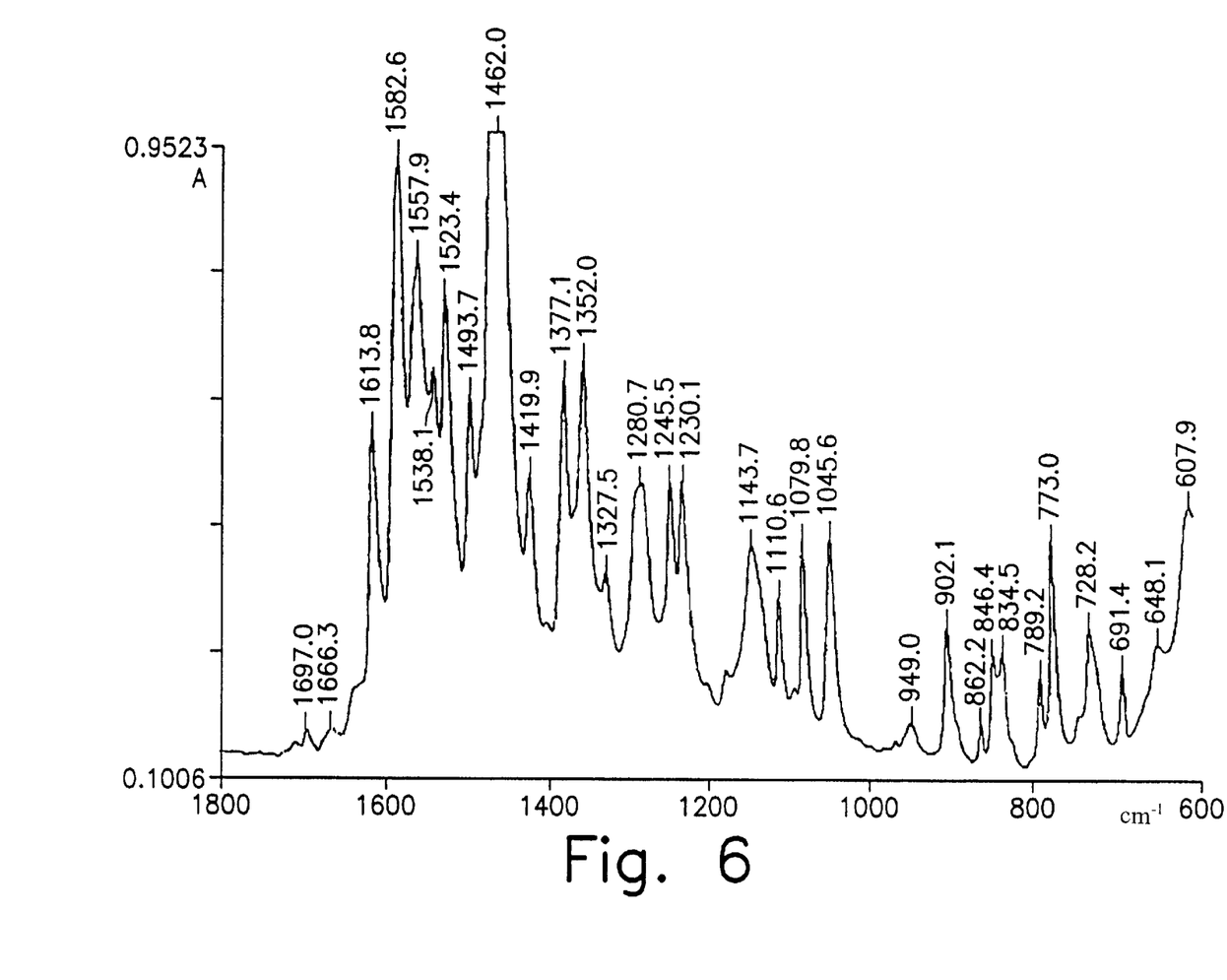
FIG. 6 is a characteristic infrared (IR) absorption spectrum of torsemide Form V.

Torsemide Form V is characterized by infra-red (IR) spectrum peaks at about 834, 846, 862, 1111, 1230, 1246, 1328, 1352, 1420, 1523, 1583, 1614 cm$^{-1}$±2, as shown in FIG. 6.

Amorphous Torsemide

Amorphous torsemide and processes for making amorphous torsemide have also been discovered.

Amorphous torsemide is prepared by suspending torsemide in water, and raising the pH with ammonia gas or ammonium hydroxide to allow the torsemide to dissolve. Ammonium hydroxide is preferred. The solution is then cooled to a temperature that allows lyophilization. Temperatures between about −50° C. to about −80° C. are suitable. Amorphous torsemide is then isolated by lyophilizing, or freeze-drying, the solution. Preferably, the lyophilization is preformed at less than about 0.1 Torr for 80 hours. By the methods of the present invention, torsemide is completely dissolved, and therefore any polymorphic form of torsemide that dissolves in water by raising the pH with ammonium hydroxide is suitable for the present process of making amorphous torsemide. The isolated amorphous torsemide has the advantage of being more soluble than crystalline forms of torsemide including but not limited to crystalline forms of torsemide reported in U.S. Pat. No. 5,914,336; U.S. Pat. No. Re. 34,672 and PCT Publication WO 00/20395.

Figure 7:
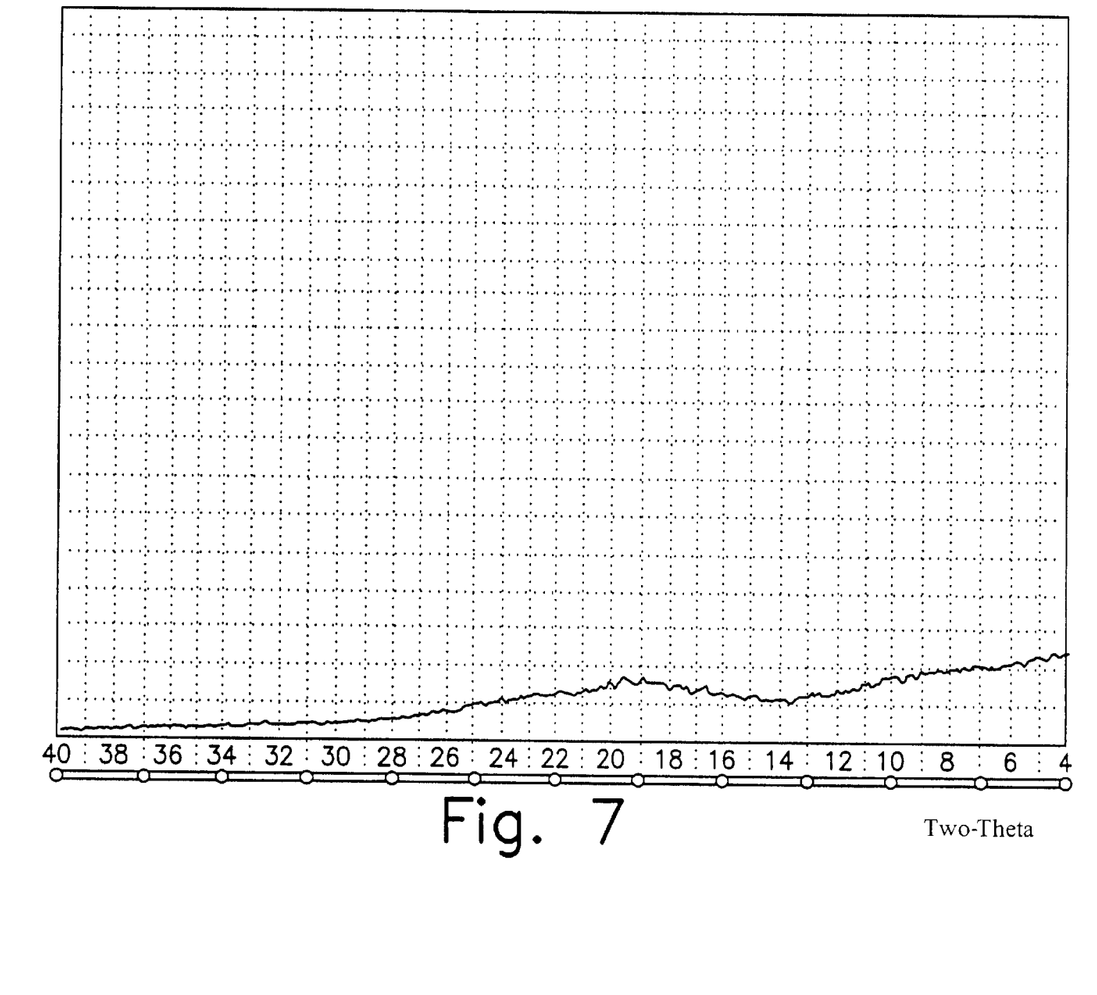
FIG. 7 is a characteristic x-ray powder diffraction spectrum of amorphous torsemide.

The x-ray powder diffraction spectrum of amorphous torsemide shown in FIG. 7. It characteristically does not show diffraction peaks and is characterized by a broad diffraction maxima at about 14 to 26 degrees two-theta.

Figure 8:
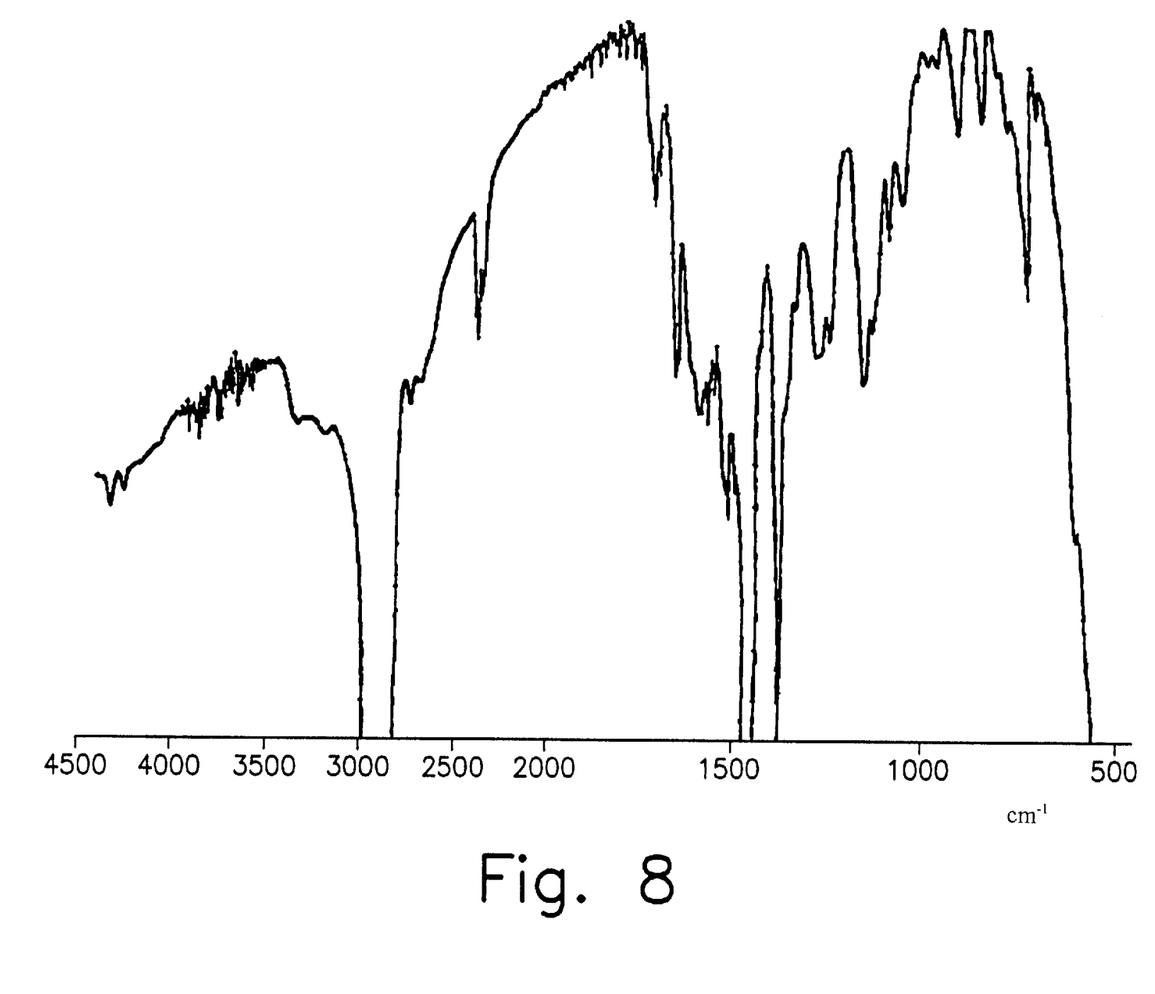
FIG. 8 is a characteristic infrared (IR) absorption spectrum of amorphous torsemide.

The IR spectrum of amorphous torsemide is characterized by typical bands at 833, 899, 1044, 1080, 1125, 1146, 1236, 1267, 1489, 1516, 1585, 1644, 1694 cm$^{-1}$±2, as shown in FIG. 8.

Figure 9:
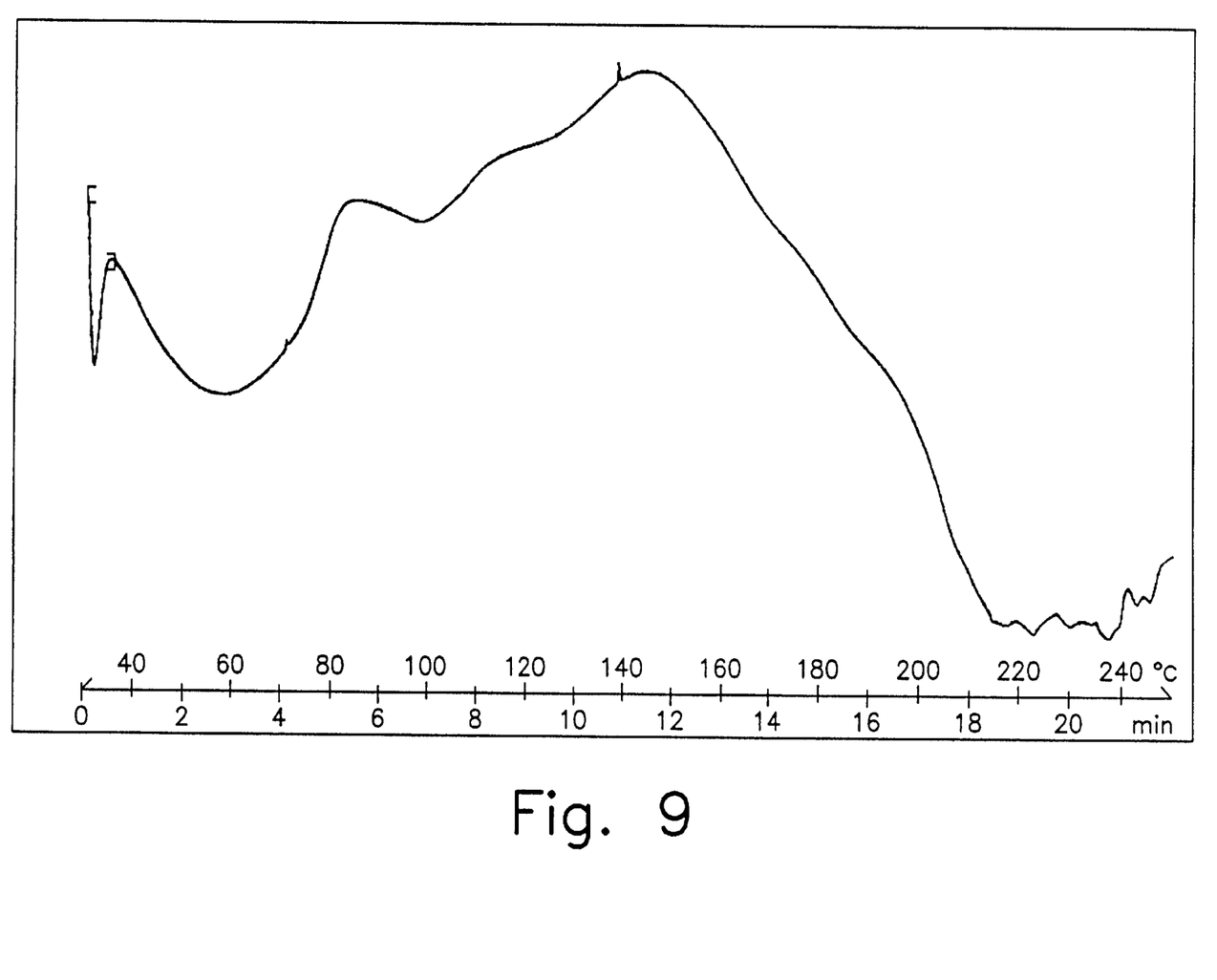
FIG. 9 is a characteristic differential scanning calorimetric (DSC) thermogram of amorphous torsemide.

The DSC thermogram for amorphous torsemide contains broad endotherms and exotherms typical of amorphous matter, as shown in FIG. 9.

In another embodiment of the present invention, amorphous torsemide is a useful intermediate in the preparation of torsemide Dupont Form 2 ethanol adduct. By the methods of the present invention amorphous torsemide is added to ethanol and the mixture is heated for a time sufficient to induce the transformation of amorphous torsemide to torsemide Dupont Form 2. The mixture is heated to about 50° C. to about 80° C. to induce the absorption of ethanol by the amorphous torsemide and to induce the evaporation of excess ethanol thereby yielding torsemide Dupont Form 2. Preferably, the mixture is heated at about 80° C. for about 7 hours.

Amorphous torsemide is a useful intermediate in the preparation of torsemide modification I and modification II, which will be discussed below.

Torsemide Modification I

The present invention also relates to a process for preparing torsemide modification I from a mixture of torsemide modification I and modification II or from torsemide modification II. As described above, torsemide modification I is defined herein as the torsemide characterized by the x-ray powder diffraction pattern of FIG. 1, in the Topfmeier Declaration. Torsemide modification II is defined herein as the torsemide characterized by the x-ray powder diffraction pattern of FIG. 2, in the Topfmeier Declaration.

By the methods of the present invention, torsemide modification I is prepared from torsemide by adding torsemide to a solvent mixture containing acetonitrile. Preferably torsemide modification I is prepared from torsemide modification II or from mixtures of torsemide modifications I and II. The mixture of torsemide and solvent is then heated to reflux with stirring for a suitable time to induce the transformation of torsemide modification II or mixtures of torsemide modifications I and II to torsemide modification I. In an embodiment of the present invention, the mixture is heated about 60° C. to about 70° C. In another embodiment of the present invention, the mixture is heated to about 65±0.5° C. The completion of the reaction is monitored by IR spectrometry. Preferably, the reaction is stirred for about 15 to 30 minutes. Torsemide modification I is isolated by filtering the hot mixture followed by drying under high vacuum. Preferably, drying is performed at less than about 1 mm Hg at a temperature of about 40 to 60° C. for a sufficient time. Drying is complete upon reaching constant weight. Preferably, the crystals are dried for about 4–6 hours.

By an alternative method of the present invention, torsemide modification I is prepared from torsemide by adding torsemide to a solvent mixture containing acetonitrile in which the mixture of torsemide and solvent is then stirred at about 20° C. to about 30° C. for a suitable time to induce the transformation of torsemide to torsemide modification I. Preferably torsemide modification I is prepared from torsemide modification II or mixtures of torsemide modifications I and II. Preferably, the reaction is stirred at room temperature until the reaction is complete. The completion of the reaction is monitored by IR spectrometry. When a solvent mixture of acetonitrile and dimethyl sulfoxide is used, the reaction is preferably stirred for about 30 to about 45 minutes. When a solvent mixture of acetonitrile and water is used, the reaction is preferably stirred for greater than 45 minutes. Torsemide modification I is isolated upon filtration and drying. The filtration may be done at a range of temperatures including from about 0° C. to about room temperature.

In an embodiment of the present invention, the solvent mixture containing acetonitrile is: acetonitrile and water where the volume ratio is between about 1:15 and 15:1. Preferably the acetonitrile to water ratio is about 5:1. In another embodiment of the present invention, the solvent mixture containing acetonitrile is: acetonitrile and dimethyl sulfoxide (DMSO) where the volume ratio is between about 1:15 and 15:1. Preferably, the acetonitrile to DMSO ratio is about 4:1.

Torsemide suitable for the preparation of torsemide modification I by the methods of the present invention includes torsemide modification II. In an alternative embodiment of the present invention, torsemide suitable for the preparation of torsemide modification I includes mixtures of torsemide modification I and modification II. In an embodiment of the present invention suitable mixtures of torsemide modification I and modification II include mixtures comprising between about 5% and 95% of modification I and between about 95% and 5% of modification II. Additionally, mixtures of torsemide modification I and II suitable for the present invention also include mixtures comprising between about 10% and 90% of modification I and between about 90% and 10% of modification II.

Additionally, mixtures of torsemide modification I and II suitable for the present invention also include mixtures comprising between about 20% and 80% of modification I and between about 80% and 20% of modification II.

Additionally, mixtures of torsemide modification I and II suitable for the present invention also include mixtures comprising between about 30% and 70% of modification I and between about 70% and 30% of modification II. Additionally, mixtures of torsemide modification I and II suitable for the present invention also include mixtures comprising between about 40% and 60% of modification I and between about 60% and 40% of modification II. Additionally, mixtures of torsemide modification I and II suitable for the present invention also include mixtures comprising about 50% of modification I and about 50% of modification II.

By an alternative method of the present invention, torsemide modification I is prepared from torsemide by adding torsemide to methanol. The mixture of torsemide and methanol is then stirred at reflux until the torsemide is completely dissolved. The solution may be then cooled to about 0 to 5° C. and stirred for an additional one to two hours. Torsemide modification I is isolated by filtration followed by drying. By the methods of the present invention, torsemide is completely dissolved in methanol, and therefore any polymorphic form of torsemide that completely dissolves in methanol at reflux temperature is suitable for the present process of making torsemide modification I. Thus, torsemide suitable for the preparation of torsemide modification I when using only methanol as the solvent includes torsemide modification I, torsemide modification II, torsemide Form V, amorphous torsemide, torsemide Dupont Form 2, torsemide Dupont Form 2 solvent adducts and torsemide solvent adducts and mixtures thereof. Preferably torsemide modification I is prepared from torsemide modification II or mixtures of torsemide modifications I and II.

By an alternative method of the present invention, torsemide modification I may be made from torsemide Dupont Form 2. By the process of the present invention, torsemide Dupont Form 2 is stirred in water at pH 5 for a time sufficient to induce the transformation of Dupont Form 2 to torsemide modification I. Preferably the mixture is stirred for 3 hours. Torsemide modification I is isolated by filtration followed by drying under high vacuum at a temperature of about 40° C. to 60° C. for a sufficient time to complete drying. Drying is complete upon reaching constant weight.

In another embodiment of the present invention, torsemide modification I may be made from torsemide modification II by reslurry in ethanol. By the process of the present invention, torsemide modification II is stirred at room temperature in ethanol for a time sufficient to induce the transformation of torsemide modification II to torsemide modification I. Preferably the mixture is stirred for 2 hours. Torsemide modification I is isolated upon filtering the mixture followed by drying under high vacuum at a temperature of about 40° C. to about 60° C. for a sufficient time to complete drying. Drying is complete upon reaching constant weight. It has been observed that torsemide modification I is stable in an ethanol slurry for at least 65 hours.

In another embodiment of the present invention, torsemide modification I may be made from torsemide modification II by reslurry in dimethyl formamide (DMF). By the methods of the present invention, torsemide modification II is stirred at room temperature in DMF for a time sufficient to induce the transformation of torsemide modification II to torsemide modification I. Torsemide modification I is isolated upon filtering the mixture followed by drying under high vacuum at a temperature of about 40° C. to about 60° C. for a sufficient time to complete drying. Drying is complete upon reaching constant weight. It has been observed that torsemide modification I is stable in an ethanol slurry for at least 65 hours.

Mixtures of Torsemide Modifications I and II

By another embodiment of the present invention, torsemide Form V is a useful intermediate for making a mixture of torsemide modifications I and II. By the methods of the present invention, torsemide Form V is added to water at pH 5. The mixture is stirred for about one hour and torsemide modifications I and II are isolated by filtration followed by drying.

Torsemide Modification II

The present invention also relates to processes for making torsemide modification II from amorphous torsemide by reslurry in water. By the processes of the present invention, amorphous torsemide is stirred at room temperature in water for a time sufficient to induce the transformation of amorphous torsemide to torsemide modification II. Complettion of the transformation is monitored by IR spectrometry. Preferably, the mixture is stirred for about 3 hours. Upon completion of the transformation, torsemide modification II is isolated upon filtering the mixture followed by drying under high vacuum at a temperature of about 40° C. to about 60° C. for a sufficient time. Drying is complete upon reaching a constant weight.

In an alternative embodiment of the present invention, torsemide modification II is made from amorphous torsemide by stirring amorphous torsemide in water at about 80° C. for a sufficient time to induce the transformation of amorphous torsemide to torsemide modification II. Completion of the conversion is monitored by IR spectrometry. Upon completion of the conversion, torsemide modification II is isolated upon filtering the mixture followed by drying under high vacuum at a temperature of about 40° C. to about 60° C. for a sufficient time. Drying is complete upon reaching a constant weight.

Torsemide used in the present invention to make torsemide Form V and amorphous torsemide may be prepared according to methods known in the art, including those described in U.S. Pat. No. Re. 30,633, the contents of which are incorporated by reference. Torsemide modification II was obtained following present Example 12 or the procedure of U.S. Pat. No. Re. 34,672.

In accordance with the present invention, these new forms of torsemide may be prepared as pharmaceutical compositions that are particularly useful for the treatment of hypertension and edema associated with congestive heart failure, renal disease, or hepatic disease. Such compositions comprise one of the new forms of torsemide with pharmaceutically acceptable carriers and/or excipients known to one of skill in the art.

Preferably, these compositions are prepared as medicaments to be administered orally, or intravenously. Suitable forms for oral administration include tablets, compressed or coated pills, dragees, sachets, hard or gelatin capsules, sub-lingual tablets, syrups and suspensions. While one of ordinary skill in the art will understand that dosages will vary according to the indication, age of the patient, etc., generally polymorphic forms and amorphous forms of torsemide of the present invention will be administered at a daily dosage of about 2 to about 200 mg per day, and preferably about 5 to about 100 mg per day.

The powder X-ray diffraction patterns were obtained by methods known in the art using a Philips X-ray powder diffractometer, Goniometer model 1050/70 at a scanning speed of 2° per minute.

The differential scanning calorimeter thermograms were obtained by methods known in the art using a DSC Mettler 821 Star$^e$. The weight of the samples was about 4 mg. The temperature range of scans was 30° C.–250° C. at a rate of 10° C./min. Samples were purged with nitrogen gas at a flow rate of 40 mL/min. Standard 40 μl aluminum crucibles were used having lids with three small holes.

The infrared spectra were obtained by methods known in the art using a Perkin Elmer FT-IR Paragon 1000 spectrometer. Samples were analyzed in Nujol mulls. Spectra were obtained at 4 cm$^{-1}$ resolution and 16 scans each.

The thermogravimetric analysis data (TGA) were obtained by methods known in the art using a TG30 Mettler Thermogravimetric Analyzer. The weight of the samples was about 9 mg. The temperature range of scans was 25° C.–200° C. at a rate of 10° C./min.

EXAMPLES

The present invention will now be further explained in the following examples. However, the present invention should not be construed as limited thereby.

Example 1
Preparation of Torsemide Dupont Form 2 Isopropanol Adduct

To a suspension of torsemide (2 g) in $H_2O$ (32 mL), 2 N NaOH was added until reaching pH 10±0.1 with stirring and the solution was filtered. Isopropyl alcohol (20 mL) was added while stirring and the solution is then acidified to pH 6±0.1 with 50% (v/v) acetic acid. The white solid was filtered, washed with water (2×10 mL) and dried under high vacuum at 50° C. for 15 hours to yield torsemide Dupont Form 2 isopropanol adduct.

Example 2
Preparation of Torsemide Dupont Form 2 Ethanol Adduct

To a suspension of torsemide (2 g) in $H_2O$ (32 mL) 2N NaOH was added until pH 10±0.1 was reached with stirring and the solution is filtered. Ethanol (20 mL) was added while stirring and the solution was then acidified to pH 6±0.1 with 50% (v/v) acetic acid. The white solid was filtered, washed with water (2×10 mL) and was dried under high vacuum at 50° C. for 15 hours to yield torsemide Dupont Form 2 ethanol adduct.

Example 3
Preparation of Torsemide Dupont Form 2 Ethanol Adduct from Amorphous Torsemide Amorphous torsemide (50 mg) was place in a drying plate or a crucible and ethanol (15 mg) was added. The crucible was then place in an oven at a temperature of 80° C. After heating for 7 hours the amorphous torsemide was converted to torsemide Dupont Form 2 ethanol adduct and all the excess ethanol had evaporated.

Example 4
Preparation of Torsemide Modification I from Torsemide Dupont Form 2

Torsemide Dupont form 2 (150 mg) was stirred in the presence of $H_2O$ (75 mL) at pH 5 for 3 hours to yield Torsemide Modification I. Torsemide modification I is isolated by filtration followed by drying under high vacuum below 0.1 Torr at 50° C.

Example 5
Preparation of Amorphous Torsemide

To a suspension of torsemide (1 g) in $H_2O$ (16 mL), ammonium hydroxide solution (24% v/v) was added with stirring until reaching pH 10±0.1 and complete dissolution. The solution was cooled to −80° C. and lyophilized under high vacuum at below 0.1 Torr for 80 hours.

Example 6
Preparation of Torsemide Form V

Ammonia gas was bubbled into a solution of torsemide (2 g) in water (32 mL) until pH 10±0.2 was reached. The solution was filtered and the pH of the filtrate was lowered to 9.2±0.2 by the addition of acetic acid until precipitation began. The solution was then stirred for an additional 30 minutes. The solid was filtered, washed with water (2×10 mL), and dried under high vacuum at 50° C. to yield torsemide Form V.

Example 7
Preparation of Torsemide Form V

Ammonia gas was bubbled into a solution of torsemide (2 g) in EtOH (20 mL) until pH 10±0.2 was reached. The solution was filtered and the filtrate was reduced under a gentle stream of nitrogen for about 10 minutes, which enhanced precipitation of the compound. The resulting white solid was filtered, washed with cold ethanol (2×5 mL) and dried under high vacuum at 50° C. to yield torsemide Form V.

Example 8
Preparation of Torsemide Form V

Ammonium hydroxide ($NH_4OH$) was added with stirring to a suspension of torsemide (2 g) in water (32 mL), until pH 10±0.1 was reached. The solution was then filtered and the pH of the filtrate was lowered to 9.2±0.2 by the addition of acetic acid until precipitation begins. The solution was stirred for an additional 30 minutes. The resulting white solid was filtered, washed with water (2×10 mL) and dried under high vacuum at 50° C. for 15 hours to yield torsemide Form V.

Example 9
Preparation of Torsemide Modification I

A 100 mL three necked flask, equipped with thermometer and a mechanical stirrer was charged with a mixture of acetonitrile:water (5:1, 26 mL), and torsemide (modification II containing less than 20% of modification I, 5 g) and stirred at 60° C. for 30 minutes. The mixture was then filtered hot and washed using the same solvent mixture (2×6.5 mL). The wet solid dried under high vacuum (3 mm Hg) at 50° C. for 6 hours to yield 4.7 g of torsemide modification I in which no torsemide modification II was detectable by IR or x-ray powder diffraction methods.

Example 10
Preparation of Torsemide Modification I

A 250 mL three necked flask, equipped with a mechanical stirrer was charged with a mixture of acetonitrile:DMSO (4:1, 100 mL), and torsemide (modification II containing less than 20% of modification I, 2 g) and stirred at 27±2 ° C. for 30 minutes. The mixture cooled to 2–3 ° C. and stirred for another 2 hours. The mixture was then filtered and dried under high vacuum (3 mm Hg) at 50° C. for 6 hours to yield 1.9 g of torsemide modification I in which no torsemide modification II was detectable by IR or x-ray powder diffraction methods.

Example 11
Preparation of Torsemide Modification I

A 250 mL three necked flask, equipped with a mechanical stirrer and a condenser was charged with methanol (200 mL), and torsemide (modification II containing less than 20% of modification I, 2 g) and stirred at reflux to complete dissolution. The mixture cooled to 2–3° C. and stirred for another 2 hours. The mixture was then filtered and dried under high vacuum (3 mm Hg) at 50° C. for 6 hours to yield 1.9 g of torsemide modification I in which no torsemide modification II was detectable by IR or x-ray powder diffraction methods.

Example 12
Preparation of Torsemide Modification II

A 5 L three necked flask equipped with a mechanical stirrer and a pH meter electrode, was charged with water (3000 L) and torsemide modification I(177 g). The pH of the solution was adjusted to 10.2±0.2 with 20% NaOH (approximately 53 mL). The solution is then filtered and the pH of the solution was adjusted with approximately 66 mL of a 1:1 acetic acid:water solution to a pH of 6.25±0.2. The white precipitate was filtered and washed with water (2×50 mL) and dried in a high vacuum oven at 50° C. for 6 hours. Torsemide modification II was isolated in 93.2% yield, 165 g.

Example 13
Preparation of Torsemide Modification II from Amorphous Torsemide

Amorphous torasemide (50 mg) left in the presence of $H_2O$ (15 mg) at 80° C. for 7 hours to yield torsemide modification II. Torsemide modification II is isolated by filtration followed by drying under high vacuum below 0.1 Torr at 50° C.

Example 14
Preparation of a Mixture of Torsemide Modification I and Modification II from Torsemide Form V Torsemide Form V (150 mg) was stirred in the presence of H20 (75 mL) at pH 5 for 1 hour to yield a mixture of Torsemide Modification II and Modification I. The mixture of torsemide modification II and modification I is isolated by filtration followed by drying under high vacuum below 0.1 Torr at 50° C.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A process for making torsemide Dupont Form 2 comprising the steps of:
   (a) suspending torsemide in water;
   (b) basifying the torsemide suspension of step (a) with sufficient base to substantially dissolve the torsemide;
   (c) adding an organic solvent to the resulting torsemide solution in an amount sufficient to induce the formation of torsemide Dupont Form 2;
   (d) adding an acid to the torsemide solution of step (c) until torsemide Dupont Form 2 begins to precipitate; and
   (e) isolating torsemide Dupont Form 2.

2. The process of claim 1, wherein the organic solvent is an alcohol selected from the group consisting of ethanol, propanol, and isopropanol.

3. The process of claim 2 wherein the solvent is isopropanol.

4. The process of claim 2 wherein the solvent is ethanol.

5. The process of claim 1 wherein the base is sodium hydroxide.

6. The process of claim 1 wherein the acid is acetic acid.

7. The process of claim 1, wherein the isolation step further comprises the steps of removing the solvent, and drying the torsemide Dupont Form 2.

8. A pharmaceutical composition comprising torsemide Dupont Form 2 and a pharmaceutically acceptable carrier.

9. A method for treating edema comprising the step of administering to a patient in need of such treatment a therapeutically effective amount of the torsemide Dupont Form 2.

10. A process for making torsemide Dupont Form 2 solvent adduct comprising the steps of:
    (a) suspending torsemide in water;
    (b) basifying the torsemide suspension of step (a) with sufficient base to substantially dissolve the torsemide;
    (c) adding an organic solvent to the resulting torsemide solution in an amount sufficient to induce the formation of torsemide Dupont Form 2 solvent adduct;
    (d) adding an acid to the torsemide solution of step (c) until torsemide Dupont Form 2 solvent adduct begins to precipitate; and
    (e) isolating torsemide Dupont Form 2 solvent adduct.

11. The process of claim 10 wherein the organic solvent is an alcohol selected from the group consisting of ethanol, propanol, and isopropanol.

12. The process of claim 11 wherein the solvent is isopropanol.

13. The process of claim 12 wherein the isolated solvent adduct is torsemide Dupont Form 2 isopropanol adduct.

14. The process of claim 11 wherein the solvent is ethanol.

15. The process of claim 14 wherein the isolated solvent adduct is torsemide Dupont Form 2 ethanol adduct.

16. The process of claim 10 wherein the base is sodium hydroxide.

17. The process of claim 10 wherein the acid is acetic acid.

18. The process of claim 10, wherein the isolation step further comprises the steps of removing the solvent, and drying the torsemide Dupont form 2 solvent adduct.

19. The product of the process of claim 11.

20. The product of the process of claim 12.

21. The product of the process of claim 14.

22. Torsemide Dupont Form 2 ethanol adduct.

23. Torsemide solvent adduct.

24. Torsemide solvent adduct wherein the solvent content is up to about 2.5% by weight.

25. Torsemide Dupont Form 2 isopropanol adduct which is characterized by a powder x-ray diffraction pattern comprising peaks at about 6.0±0.2, 9.2±0.2, 9.7±0.2, 11.3±0.2, 12.0±0.2, 15.8±0.2, 18.4±0.2, 19.7±0.2, 20.4±0.2, 22.6±0.2, 23.5±0.2, 25.5±0.2, and 27.5±0.2 degrees two-theta.

26. A pharmaceutical composition comprising torsemide Dupont Form 2 ethanol adduct and a pharmaceutically acceptable carrier.

27. A pharmaceutical composition comprising torsemide Dupont Form 2 isopropanol adduct and a pharmaceutically acceptable carrier.

28. A pharmaceutical composition comprising torsemide Dupont Form 2 solvent adduct and a pharmaceutically acceptable carrier.

29. A method for treating edema comprising the step of administering to a patient in need of such treatment a therapeutically effective amount of the torsemide Dupont Form 2 isopropanol adduct.

30. A method for treating edema comprising the step of administering to a patient in need of such treatment a therapeutically effective amount of the torsemide Dupont Form 2 ethanol adduct.

31. A method for treating edema comprising the step of administering to a patient in need of such treatment a therapeutically effective amount of the torsemide Dupont Form 2 solvent adduct.

32. A process for making torsemide Dupont Form 2 ethanol adduct from amorphous torsemide comprising the steps of:
(a) suspending amorphous torsemide in ethanol;
(b) heating the suspension to 80° C.; and
(c) isolating torsemide Dupont Form 2 ethanol adduct.

33. A process for making torsemide modification I from torsemide Dupont Form 2 comprising the steps of:
(a) suspending torsemide Dupont Form 2 in water at pH 5; and
(b) isolating torsemide modification I.

34. A process for making torsemide Form V comprising the steps of:
(a) suspending torsemide in a solvent;
(b) increasing the pH of the torsemide suspension with base sufficient to substantially dissolve the torsemide;
(c) precipitating torsemide Form V from the resulting solution; and
(d) isolating torsemide Form V.

35. The process of claim 34 wherein the precipitation of torsemide Form V in step (c) is induced by decreasing the pH of torsemide solution by adding an amount of an acid sufficient to induce the precipitation.

36. The process of claim 34 wherein the solvent is selected from the group consisting of water and ethanol.

37. The process of claim 36 wherein the solvent is water.

38. The process of claim 36 wherein the solvent is ethanol.

39. The process of claim 34 wherein the base is selected from the group consisting of ammonia and ammonium hydroxide.

40. The process of claim 39 wherein the base is ammonia.

41. The process of claim 35 wherein the acid is acetic acid.

42. The process of claim 34 wherein the solution of step (c) is filtered.

43. The process of claim 34 wherein the precipitation of torsemide Form V in step (c) is induced by reducing the resulting solution under a stream of inert gas for a time sufficient to induce the precipitation.

44. The product of the process of claim 34.

45. Torsemide which is characterized by a powder x-ray diffraction pattern comprising peaks at about: 5.9±0.2, 8.4±0.2, 12.0±0.2, 12.5±0.2, 13.30±0.2, 16.0±0.2, 17.7±0.2, 19.9±0.2, 21.5±0.2, 22.7±0.2, 24.0±0.2, 24.7±0.2 degrees two-theta.

46. A pharmaceutical composition comprising the torsemide Form V, and a pharmaceutically acceptable carrier.

47. A method for treating edema comprising the step of administering to a patient in need of such treatment a therapeutically effective amount of the torsemide Form V.

48. A process for making amorphous torsemide comprising the steps of:
(a) suspending torsemide in water;
(b) treating the torsemide suspension of step (a) with ammonium hydroxide or ammonium gas sufficient to completely dissolving the torsemide;
(c) cooling the torsemide solution of step (b); and
(d) isolating amorphous torsemide by lyophilization.

49. The process of claim 48, wherein the torsemide solution of step (c) is cooled to about −50° C. to about −80° C.

50. The process of claim 48 wherein the base is ammonium hydroxide.

51. The product of the process of claim 48.

52. Amorphous torsemide, which is characterized by a broad x-ray diffraction maxima at about 14 to 26 degrees two-theta and an IR spectrum comprising bands at 833, 899, 1044, 1080, 1125, 1146, 1236, 1267, 1489, 1516, 1585, 1644, 1700cm$^{-1}$±2.

53. A pharmaceutical composition comprising amorphous torsemide and a pharmaceutically acceptable carrier.

54. A method for treating edema comprising the step of administering to a patient in need of such treatment a therapeutically effective amount of amorphous torsemide.

55. A process for making torsemide modification I comprising the steps of:
(a) adding torsemide to a solvent mixture comprising acetonitrile; and
(b) isolating torsemide modification I.

56. The process of claim 55 wherein the mixture of torsemide and solvent is heated.

57. The process of claim 56 wherein the mixture is heated up to about reflux.

58. The process of claim 55 wherein the solvent mixture comprising acetonitrile is acetonitrile and water.

59. The process of claim 58 wherein the mixture of torsemide and solvent is heated to about 40° C. to about 60° C.

60. The process of claim 58 wherein the solvent mixture has an acetonitrile to water ratio of about 5:1.

61. The process of claim 55 wherein the solvent mixture comprising acetonitrile is acetonitrile and dimethyl sulfoxide.

62. The process of claim 61 wherein the mixture of torsemide and solvent is stirred at a temperature between about 20° C. to about 30° C.

63. The process of claim 61 wherein the solvent mixture has an acetonitrile to dimethyl sulfoxide ratio of about 4:1.

64. The process of claim 55 wherein the torsemide of step (a) is torsemide modification II.

65. The process of claim 55 wherein the torsemide of step (a) is a mixture of torsemide modification I and torsemide modification II.

66. The process of claim 65 wherein the mixture of torsemide comprises between about 5% and 95% of torsemide modification I and between about 9% and 5% of torsemide modification II.

67. The process of claim 66 wherein the mixture of torsemide comprises between about 10% and 90% of torsemide modification I and between about 900% and 10% of torsemide modification II.

68. The process of claim 67 wherein the mixture of torsemide comprises between about 50% of torsemide modification I and about 50% of torsemide modification II.

69. A pharmaceutical composition comprising torsemide modification I prepared according to the process of claim 55 and a pharmaceutically acceptable carrier.

70. A process for making torsemide modification I comprising the steps of:
(a) adding torsemide to methanol;
(b) refluxing the mixture of torsemide and methanol; and
(c) isolating torsemide modification I.

71. The process of claim 70 further comprising the step of cooling said mixture of torsemide and methanol to about 0° C. to about 5° C.

72. The process of claim 70 wherein the torsemide of step (a) is torsemide modification II.

73. The process of claim 70 wherein the torsemide of step (a) is a mixture of torsemide modification I and torsemide modification II.

74. The process of claim 73 wherein the mixture of torsemide comprises between about 5% and 95% of torsemide modification I and between about 95% and 5% of torsemide modification II.

75. The process of claim 74 wherein the mixture of torsemide comprises between about 10% and 90% of torsemide modification I and between about 90% and 10% of torsemide modification II.

76. The process of claim 75 wherein the mixture of torsemide comprises between about 50% torsemide modification I and about 50% torsemide modification II.

77. The process of claim 70 wherein the torsemide of step (a) is torsemide Form V.

78. The process of claim 70 wherein the torsemide of step (a) is amorphous torsemide.

79. The process of claim 70 wherein the torsemide of step (a) is torsemide Dupont Form 2 isopropanol adduct.

80. A pharmaceutical composition comprising torsemide modification I prepared according to the process of claim 70 and a pharmaceutically acceptable carrier.

81. A process for making torsemide modification II comprising the steps of:
    (a) suspending amorphous torsemide in water;
    (b) heating the suspension; and
    (c) isolating torsemide modification II.

82. The process of claim 81 wherein the torsemide modification II is isolated by filtration followed by drying.

83. A process for making a mixture of torsemide modification I and torsemide modification II comprising the steps of:
    (a) suspending torsemide Form V in water; and
    (b) isolating a mixture of torsemide modification I and torsemide modification II.

84. The process of claim 83 wherein the pH of the water is about 5.

85. A processes for making torsemide modification II comprising the steps of:
    (a) adding amorphous torsemide to water;
    (b) stirring the torsemide water mixture for a time sufficient to induce the transformation of amorphous torsemide to torsemide modification II; and
    (c) isolating torsemide modification II.

86. The process of claim 85 further comprising the step of heating the torsemide mixture.

87. The process of claim 86 wherein the mixture is heated to about 80° C.

88. A process for making torsemide modification I comprising the steps of:
    (a) adding torsemide modification II to ethanol;
    (b) stirring the torsemide ethanol mixture for a time sufficient to induce the transformation of torsemide modification II to torsemide modification I; and
    (c) isolating torsemide modification I.

89. A process for making torsemide modification I comprising the steps of:
    (a) adding torsemide modification II to dimethyl formamide;
    (b) stirring the mixture of torsemide modification II and dimethyl formamide for a time sufficient to induce the transformation of torsemide modification II to torsemide modification I; and
    (c) isolating torsemide modification I.

90. Torsemide Dupont Form 2 ethanol adduct which is characterized by a powder x-ray diffraction pattern comprising peaks at about 6.0±0.2, 9.2±0.2, 9.7±0.2, 11.3±0.2, 12.0±0.2, 15.8±0.2, 18.4±0.2, 19.7±0.2, 20.4±0.2, 22.6±0.2, 23.5±0.2, 25.5±0.2, and 27.5±0.2 degrees two-theta.

91. The process of claim 40 wherein the ammonia is a gas.

* * * * *